US008652126B2

(12) United States Patent
Rantala

(10) Patent No.: US 8,652,126 B2
(45) Date of Patent: Feb. 18, 2014

(54) METHOD AND COMPUTER PROGRAM FOR AUTHENTICATING A PHYSIOLOGICAL SENSOR, A SENSOR SYSTEM, A PATIENT MONITOR, AND A PHYSIOLOGICAL SENSOR

(75) Inventor: Borje Rantala, Helsinki (FI)

(73) Assignee: General Electric Company, Schenectady, NY (US)

( * ) Notice: Subject to any disclaimer, the term of this patent is extended or adjusted under 35 U.S.C. 154(b) by 923 days.

(21) Appl. No.: 12/624,469

(22) Filed: Nov. 24, 2009

(65) Prior Publication Data
US 2011/0125000 A1 May 26, 2011

(51) Int. Cl.
*A61B 18/18* (2006.01)
(52) U.S. Cl.
USPC .............................................. 606/34; 606/38
(58) Field of Classification Search
USPC .................................... 606/32, 34, 38
See application file for complete search history.

(56) References Cited

U.S. PATENT DOCUMENTS

| 5,383,874 | A | * | 1/1995 | Jackson et al. ............ 606/1 |
|---|---|---|---|---|
| 6,165,173 | A | * | 12/2000 | Kamdar et al. ............ 606/34 |
| 6,298,255 | B1 | * | 10/2001 | Cordero et al. ............ 600/372 |
| 6,595,930 | B2 | * | 7/2003 | Rosenheimer ............ 600/561 |
| 6,622,050 | B2 | | 9/2003 | Thompson ............ 607/60 |
| 6,676,600 | B1 | * | 1/2004 | Conero et al. ............ 600/438 |
| 7,048,687 | B1 | * | 5/2006 | Reuss et al. ............ 600/300 |
| 7,248,910 | B2 | * | 7/2007 | Li et al. ............ 600/323 |
| 7,465,301 | B2 | * | 12/2008 | Bek et al. ............ 606/34 |
| 7,522,949 | B2 | | 4/2009 | Berson et al. |
| 8,308,355 | B2 | * | 11/2012 | Lane et al. ............ 374/153 |
| 2003/0106930 | A1 | * | 6/2003 | Williams ............ 235/103 |
| 2003/0116159 | A1 | * | 6/2003 | Orr et al. ............ 128/204.23 |
| 2006/0161054 | A1 | | 7/2006 | Reuss et al. |
| 2007/0043275 | A1 | * | 2/2007 | Manheimer et al. ............ 600/323 |
| 2011/0034910 | A1 | * | 2/2011 | Ross et al. ............ 606/1 |

FOREIGN PATENT DOCUMENTS

| DE | 102005011385 A1 | 12/2005 |
|---|---|---|
| WO | 2008/021920 A2 | 2/2008 |
| WO | 2008/054980 A2 | 5/2008 |

OTHER PUBLICATIONS

EP Search Report and Written Opinion from corresponding EP Application No. 10191259.0 on Mar. 8, 2011.

* cited by examiner

*Primary Examiner* — Linda Dvorak
*Assistant Examiner* — Jocelyn D Ram
(74) *Attorney, Agent, or Firm* — Andrus Intellectual Property Law, LLP

(57) ABSTRACT

A mechanism for authenticating a physiological sensor is disclosed. When a sensor is connected to a monitor, the monitor examines whether a first sensor-specific usage identifier of the connected sensor is consistent with a second sensor-specific usage identifier thereof. The first and second sensor-specific usage identifiers are indicative of the cumulative usage of the connected sensor, but may nevertheless be unequal. The first sensor-specific usage identifier is maintained in the sensor and the second sensor-specific usage identifier in a host memory external to the sensor. The use of the connected sensor is allowed when the examining indicates that the said two identifiers of the connected sensor are consistent, and rejected when the identifiers are inconsistent. The two identifiers are further updated in response to the use of the connected sensor in the patient monitor, thereby to keep the said identifiers consistent and updated for a subsequent use attempt of the sensor.

13 Claims, 3 Drawing Sheets

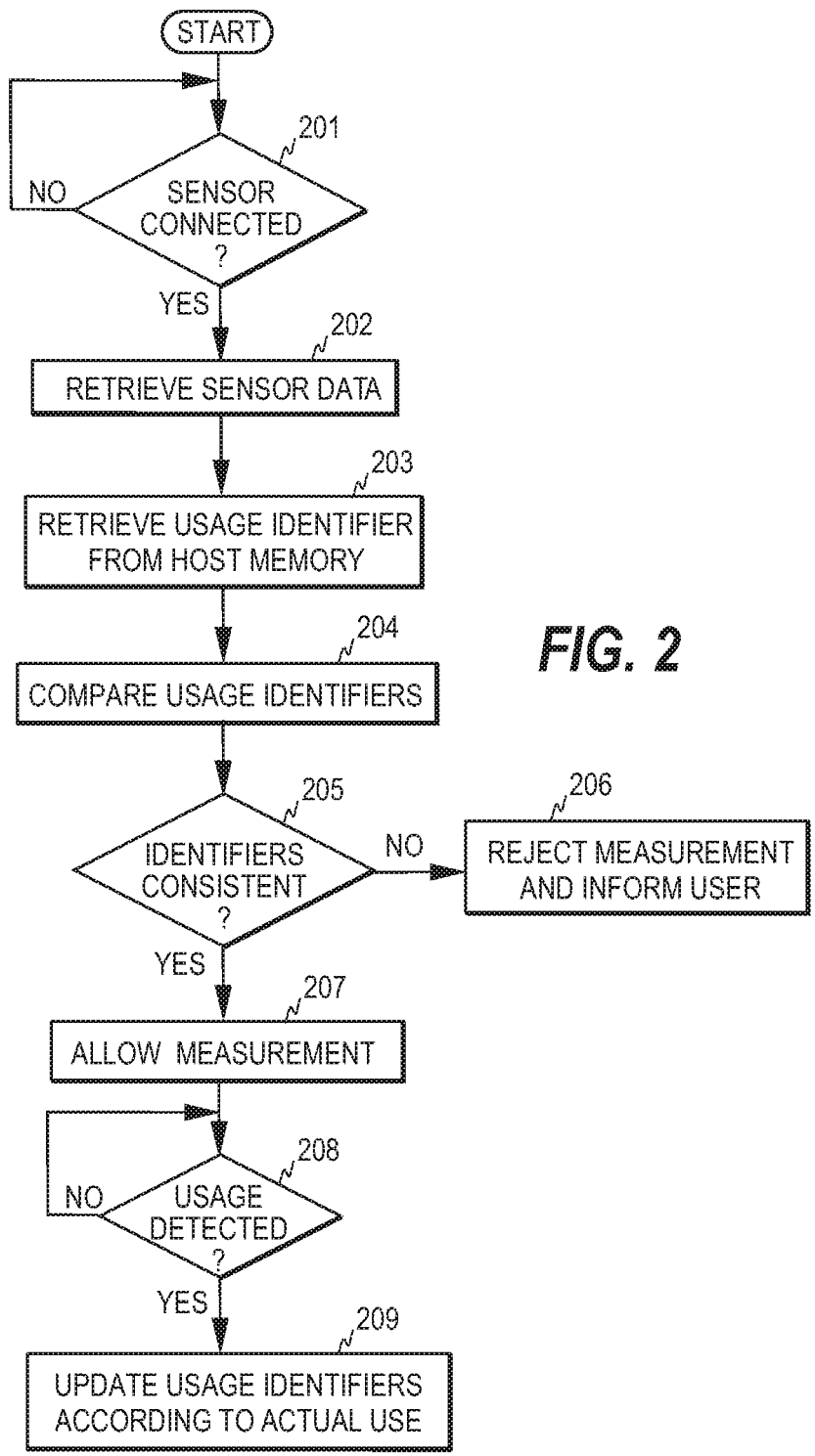

METHOD AND COMPUTER PROGRAM FOR AUTHENTICATING A PHYSIOLOGICAL SENSOR, A SENSOR SYSTEM, A PATIENT MONITOR, AND A PHYSIOLOGICAL SENSOR

BACKGROUND OF THE INVENTION

This disclosure relates generally to patient monitors and physiological sensors used for acquiring electrophysiological signals from a subject. More particularly, this disclosure relates to a detection or protection mechanism that may be employed to detect non-authentic and/or unauthorized sensors and to prevent the use of such sensors in patient monitors.

A prerequisite of patient care is that accurate and reliable measurements can be made from the patient to evaluate the patient's state. Since a patient monitor connected to a sensor may perform rather complex calculations based on the physiological signals acquired through the sensor and since the results obtained may depend on a variety of parameters related to the sensor, it is important that the sensor fulfills certain quality standards and is thus authorized to be used in the patient monitor for the measurement in question. The use of low quality sensors may lead to inaccurate and/or unreliable results, which may in turn contribute to incorrect medical decisions and even risk patient safety. It is therefore common practice to provide a sensor/monitor system with a detection mechanism that detects unauthorized and/or counterfeited sensors that may involve, if used in a patient monitor, the above drawbacks and risks.

In order to keep the sensors technically uncomplex and the production costs low, it is desirable to use a generic memory sensor, i.e. a sensor that does not include any intelligence or data processing capability for its validation and for preventing the use of unauthorized sensors in connection with the patient monitor. A generic memory sensor thus here refers to a sensor provided with a generic memory from which the patient monitor may read data and into which the monitor may write updated data. That is, the sensor memory is a plain memory with no customized parts and with no associated intelligence or data processing capability. The intelligence is typically in the patient monitor which may retrieve the sensor memory data for various purposes, process the data, and store updated data into the sensor memory.

One common way to impede illegal copying of the sensors is to make each sensor different by using a sensor-specific identifier in each sensor. This is typically a non-erasable serial number stored in the sensor memory. The serial number may be written in the memory already at the manufacture stage of the memory. Various encryption mechanisms may also be used for encrypting the sensor memory data or part thereof, and the serial number may serve as the seed value for the encryption. Encryption effectively prohibits any such copying of the sensor that calls for preceding decryption of the sensor memory data.

In addition to the sensors being provided with an encrypted memory, the patient monitors may be provided with various verification algorithms for verifying that an authorized sensor is connected to the monitor.

In one sensor system, the associated monitor is provided with authentication software for authenticating the sensor connected to the monitor. The sensor includes a memory that may include various information concerning the origin and manufacture of the sensor, such as a manufacturer code, the sensor serial number, the sensor type code, and the usage count. All or part of the memory content may be in encrypted form. The monitor uses the data stored in the sensor to authenticate the sensor. If the sensor cannot be authenticated, the monitor software prohibits the use of the sensor in the monitor. The monitor may also use the serial number to maintain a usage counter for each sensor that is authenticated by the monitor. The value of the usage counter, i.e. the number of times that the sensor has been authenticated, provides a defense mechanism against multiple unauthorized sensors manufactured with the same serial number. A mirror usage counter is maintained in the sensor memory and the sensor and monitor usage counters are synchronized to the minimum of uses remaining between the two. The usage count thus reflects the sum of all prior sensor usage independent of the monitor. That is, the number of times that a sensor with a certain serial number can be used can be limited to a certain maximum that may be set in view of the lifetime of the sensor.

Various other data security mechanisms may also be used between the sensor and the monitor. For example, digital signatures stored in the sensor memory and cryptographic hash values (message digests) determined by the monitor may be used to verify both the authenticity of the sensor and the integrity of the sensor memory data.

A major drawback related to the use of the generic memory sensors is that there are no efficient technical mechanisms to prevent the use of sensors which have been copied without first decrypting the sensor memory data. Copying a memory can be done without any understanding of the memory content, and encryption does not help as such. That is, if a binary bulk copy is taken from the original sensor memory data, the copied sensor may be connected to the associated patient monitor without the monitor detecting that the sensor is actually an unauthorized sensor.

BRIEF DESCRIPTION OF THE INVENTION

The above-mentioned problems are addressed herein which will be comprehended from the following specification.

In an embodiment, a method for authenticating a physiological sensor connected to a patient monitor comprises examining, in response to a sensor being connected to a patient monitor, whether a first sensor-specific usage identifier of the connected sensor is consistent with a second sensor-specific usage identifier of the connected sensor, wherein the first and second sensor-specific usage identifiers are indicative of cumulative usage of the connected sensor and wherein the first sensor-specific usage identifier is stored in the connected sensor and the second sensor-specific usage identifier is stored in a host memory external to the connected sensor. The method also includes allowing use of the connected sensor in the patient monitor when the examining indicates that the first and second sensor-specific usage identifiers of the connected sensor are consistent and rejecting the use of the connected sensor in the patient monitor when the examining indicates that the first and second sensor-specific usage identifiers of the connected sensor are inconsistent. The method also includes updating the first and second usage identifiers of the connected sensor in response to the use of the connected sensor in the patient monitor, thereby to keep the first and second sensor-specific usage identifiers of the connected sensor consistent and updated for a subsequent use attempt of the connected sensor.

In another embodiment, a sensor system comprises a plurality of physiological sensors, each sensor comprising a memory storing a first sensor-specific usage identifier indicative of cumulative usage of the sensor. The sensor system also includes at least one patient monitor and at least one host memory external to the plurality of physiological sensors, each host memory being accessible to at least one of the at least one patient monitor. Each of the at least one patient monitor is configured to (1) examine whether the first sensor-specific usage identifier of a sensor connected to the patient monitor is consistent with a second sensor-specific usage identifier of said sensor, wherein the second sensor-specific usage identifier is stored in at least one of the at least one host memory, (2) allow use of the connected sensor in the patient monitor when the first and second sensor-specific usage identifiers are consistent, (3) reject the use of the connected sensor in the patient monitor when the first and second sensor-specific usage identifiers are inconsistent, and (4) update the first and second usage identifiers of the connected sensor in response to the use of the connected sensor, thereby to keep the first and second sensor-specific usage identifiers of the connected sensor consistent and updated for a subsequent use attempt of the connected sensor in any of the at least one patient monitor.

In a still another embodiment, a patient monitor comprises a first interface for connecting a physiological sensor to the patient monitor and a retrieval unit configured to retrieve, upon connection of the physiological sensor to the patient monitor, a first usage identifier of the connected sensor from said sensor and a second usage identifier of the connected sensor from a host memory external to the connected sensor, wherein the first and second usage identifiers are indicative of cumulative usage of the connected sensor. The patient monitor also includes a comparison unit configured to examine whether the retrieved first and second usage identifiers of the connected sensor are consistent and a decision-making unit configured to allow use of the connected sensor in the patient monitor when the first and second usage identifiers are consistent and to reject the use of the connected sensor in the patient monitor when the first and second usage identifiers are inconsistent. The patient monitor further includes an update unit configured to update the first and second usage identifiers of the connected sensor in response to the use of the connected sensor, thereby to keep the first and second usage identifiers of the connected sensor consistent and updated for a subsequent use attempt of the sensor.

In a further embodiment, a physiological sensor attachable to a subject for acquiring a physiological measurement signal from the subject comprises a sensor element unit configured to output an electrophysiological signal, a sensor memory storing a first sensor-specific usage identifier indicative of cumulative usage of the sensor, and a memory access interface for enabling a patient monitor operably connected to the sensor to compare the first sensor-specific usage identifier with a second sensor-specific usage identifier maintained outside the sensor, thereby to enable authentication of the sensor through the comparison, wherein the second sensor-specific usage identifier is also indicative of cumulative usage of the sensor.

In a still further embodiment, a computer program product for authenticating a physiological sensor connected to a patient monitor comprises a first program product portion configured retrieve, upon connection of a sensor to a patient monitor, a first usage identifier of the connected sensor from said sensor and a second usage identifier of the connected sensor from a host memory external to the connected sensor, wherein the first and second usage identifiers are indicative of cumulative usage of the connected sensor, and a second program product portion configured to examine whether the retrieved first and second usage identifiers of the connected sensor are consistent. The computer program product further includes a third program product portion configured to allow use of the connected sensor when the first and second usage identifiers are consistent and to reject the use of the connected sensor when the first and second usage identifiers are inconsistent and a fourth program product portion configured to update the first and second usage identifiers of the connected sensor in response to the use of the connected sensor, thereby to keep the first and second usage identifiers of the connected sensor consistent and updated for a subsequent use attempt of the sensor Various other features, objects, and advantages of the invention will be made apparent to those skilled in the art from the following detailed description and accompanying drawings.

BRIEF DESCRIPTION OF THE DRAWINGS

FIG. 2 illustrates an embodiment of the operation of the sensor verification algorithm of the embodiment of FIG. 1;

DETAILED DESCRIPTION OF THE INVENTION

Figure 1:
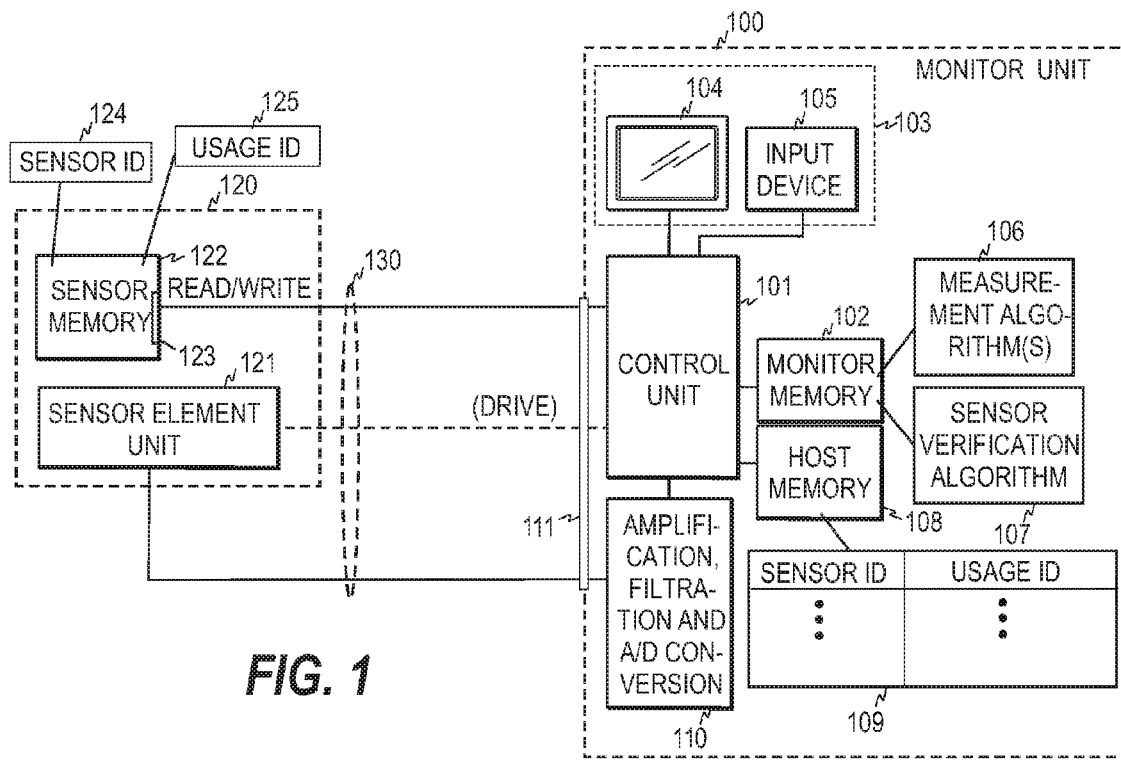
FIG. 1 is a block diagram illustrating an embodiment of the sensor system.

FIG. 1 illustrates one embodiment of a sensor and monitor system that is configured to verify the authenticity of a sensor unit connected to a monitor unit. The sensor system of FIG. 1 comprises a monitor unit 100 and a sensor unit 120 attachable to a subject (not shown). The sensor unit 120 is normally connected to the monitor unit 100 through a cable 130, but the connection may also be wireless. It is to be noted that the system is here discussed with respect to one monitor unit 100 and one sensor unit 120 connected to the monitor unit. However, the entire system typically includes several sensor units 120 and one or more monitor units 100.

The monitor unit 100 may be conceived to comprise three basic elements: a computerized control and processing unit 101, a memory 102 for the control and processing unit, and a user interface 103, which typically comprises a display 104 and one or more user input devices 105.

A reception branch 110 of the monitor unit is adapted to receive the electrophysiological signals from the sensor. The reception branch typically comprises an input amplifier, a band-pass filter, and an A/D converter (not shown). The digitized signal output from the A/D converter is supplied to the control and processing unit 101, which processes the signal data and displays the analysis results on the screen of the display. The memory of the control and processing unit holds the measurement algorithm(s) 106 needed to process the data received from the sensor unit.

The sensor unit of FIG. 1 comprises a sensor element unit 121 and a sensor memory 122. As discussed below, the sensor element unit typically comprises an array of electrodes that may be attached onto the skin of the subject. The sensor memory is a generic memory from which the monitor may read data and into which the monitor may write data through a memory access interface 123. The sensor memory is thus a plain (non-volatile) memory with no customized areas/parts, associated intelligence, or data processing capability. The memory may be, for example, an EEPROM or an EPROM memory. The memory holds a sensor-specific identifier 124 that unambiguously identifies the sensor and a sensor-specific usage identifier 125 that is indicative of the cumulative usage of the sensor. The sensor-specific identifier may be, for example, the serial number of the sensor. The usage identifier may be, for example, a usage count that indicates the total number of times the sensor unit has been used. The unique sensor-specific identifier may be stored at the manufacture stage of the memory or the sensor, and the usage identifier may be set to an initial value of zero at the manufacture stage of the sensor.

The memory 102 of the control and processing unit further holds a sensor verification algorithm 107 that is executed by the control and processing unit when a sensor is connected to the monitor unit 100. The operation of the verification algorithm is discussed below as if no encryption or any other data security mechanisms were involved. However, it is to be noted that the sensor memory data may be in encrypted form and various known data security mechanisms may be used to encrypt/decrypt the sensor memory data and/or to verify the authenticity of the sensor and/or the integrity of the sensor memory data. The sensor verification algorithm may therefore include various data security mechanisms, in addition to the basic verification mechanism applied to plain data, i.e. non-encrypted data.

The monitor unit 100 is further provided with a host memory 108 which is here presented as a separate memory unit but which may also be a memory area of the monitor memory 102. The host memory contains the sensor-specific identifiers and sensor-specific usage identifiers for all sensors that have been used together with the monitor unit, i.e. that have been authenticated successfully by the monitor unit. This information may be in the form of a look-up table 109, for example. However, the look-up table or the host memory may also include further sensor-specific information needed by the sensor verification algorithm, such as the security parameters related to the possible data security mechanisms involved. For each authorized sensor the system thus includes two usage identifiers, one in the sensor and the other outside the sensor in a memory accessible by the monitor unit(s). As discussed below, inconsistency between the two usage identifiers is indicative of an unauthorized sensor. The system may also create the usage identifier pair in connection with the first use of a sensor, if both the sensor memory data and the host memory data indicate that the sensor has not been used before. As discussed below, the two usage identifiers of an authorized sensor may be unequal even though they are consistent with each other. That is, unequal usage identifiers are not necessarily inconsistent, although equal usage identifiers of a sensor are always consistent.

FIG. 2 illustrates an embodiment of the operation of the monitor unit in terms of sensor validation/authentication. The control and processing unit constantly monitors, if a sensor is connected to the monitor unit (step 201). When the control and processing unit detects that a sensor is connected to the monitor unit (step 201/yes), the control and processing unit retrieves at least part of the sensor memory data in step 202. This data includes the sensor-specific identifier and the usage identifier stored in the sensor memory. The control and processing unit then retrieves from the host memory the usage identifier that corresponds to the sensor-specific identifier (step 203) and compares it with the usage identifier obtained from the sensor memory (step 204), thereby to check whether the two usage identifiers are consistent (step 205). If this is the case, measurement is allowed (step 207). The measurement may then start and when actual usage is detected (step 208), the two usage identifiers of the sensors are updated according to the actual use (step 209). The update may be carried out in various phases of the measurement session, prior to the disconnection of the sensor from the monitor. For example, if the usage identifiers indicate the number of times the sensor has been used, the usage identifiers may be updated any time after step 207 and before the disconnection of the sensor from the monitor at the end of the measurement session. However, if the usage identifiers indicate, for example, the total use time, the update is to be carried out after the measurement but before the disconnection of the sensor.

If steps 204 and 205 indicate that the two usage identifiers are inconsistent, the measurement is rejected and the user is informed of the situation (step 206). If the two usage identifiers are inconsistent, it is likely that an unauthorized sensor is connected to the monitor, and the user may be informed accordingly.

Figure 3:
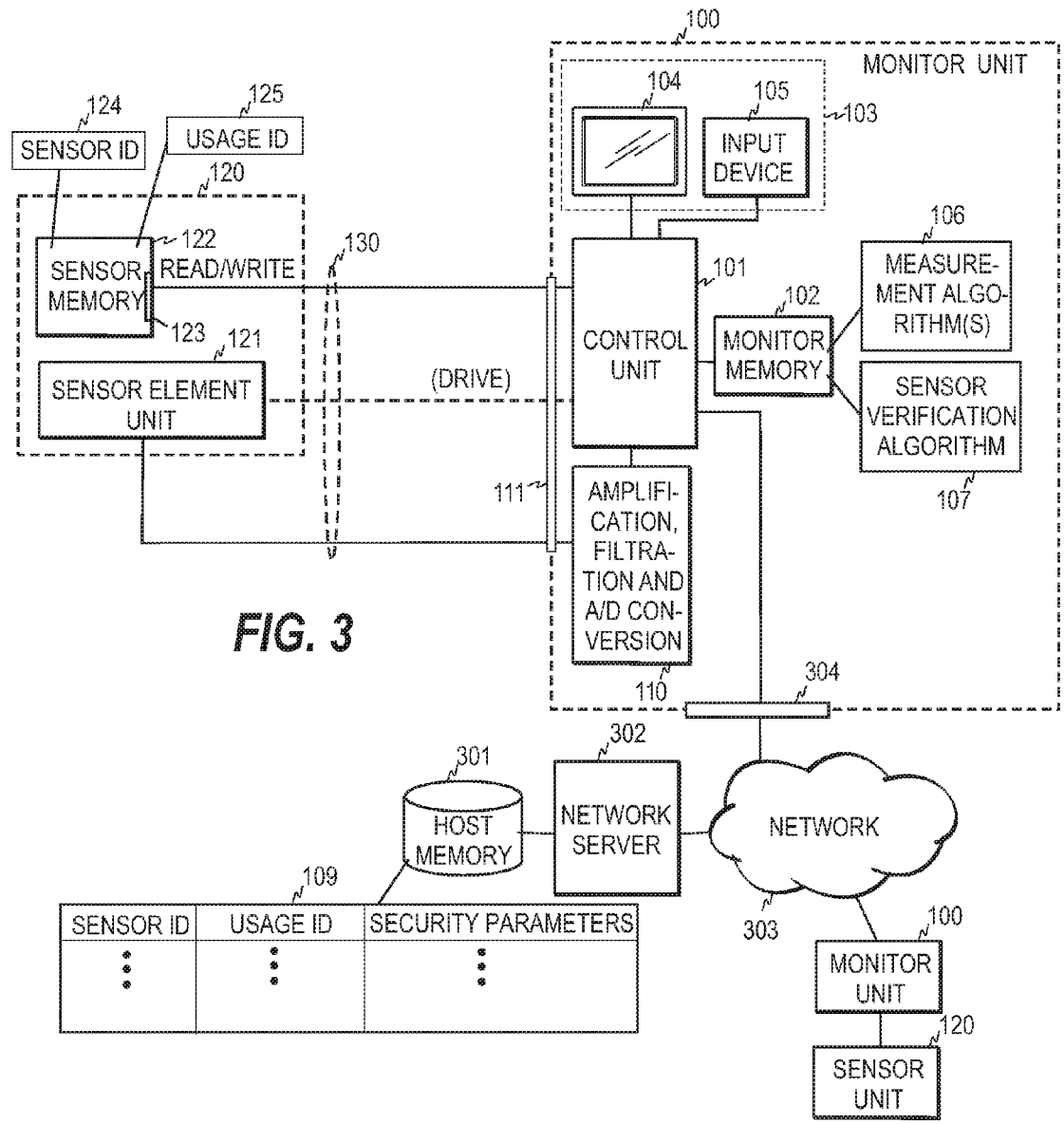
FIG. 3 illustrates another embodiment of the sensor system.

The host memory may also be in an external host device that may be accessed by several monitors through a network. This may be the case especially if the sensor may be used in several monitors. As is shown in FIG. 3, the host memory 301 may be in conjunction with a network element, such as a database server 302, through which the host memory may be accessed by a plurality of monitor units connected to the same network 303 as the server. The network may be a local area network, such as a hospital network, a wide area network, or the Internet, for example. Each monitor unit is provided with a network interface 304 and a suitable transmission protocol for reading from and writing to the host memory 301.

It is worth noting that the two usage identifiers of a sensor unit need not necessarily be equal/identical to be regarded as consistent. Instead of maintaining a centralized usage identifier in a centralized host memory 301, each of the plurality of monitor units may maintain a dedicated usage count for each sensor that is used in the monitor unit. Thus, in this embodiment each sensor unit includes a usage count indicative of the total number of times the sensor unit is used and each monitor unit includes a usage count indicative of the total number of times the sensor unit is used in that monitor unit. Inconsistency is in this embodiment detected if the usage count in the sensor unit is smaller than the usage count in the monitor unit. When an original (authorized) sensor is connected to a monitor unit for the first time, it operates normally, since the usage count in the sensor (zero) is not smaller than the usage count in the monitor (also zero). As a result of the use, the usage counts in the sensor and in the said monitor are incremented to one. If the same sensor is next connected to another monitor, the usage counts in the sensor and in the monitor are one and zero, respectively. Since the usage count in the sensor is not smaller than the usage count in the monitor, the use of the sensor is allowed. The usage count in the sensor is incremented to two and the usage count in the monitor to one. If an unauthorized copy of the sensor, in which the value of the usage count is zero, is now connected to any of these two monitors, the usage count in the sensor is smaller than the usage count in the monitor and inconsistency is detected at steps 204 and 205. Consequently, the use of the sensor is prohibited.

Thus, it is also to be noted that even if the two usage identifiers of a sensor are both indicative of the cumulative usage of the said sensor, the said identifiers are not necessarily equal in all embodiments, but each sensor-specific usage identifier stored outside the sensor, i.e. in a host memory, may be indicative of the total usage of the sensor in a given monitor unit, while the usage identifier stored in the sensor is indicative of the total usage of the sensor in all monitor units. This may the case regardless of whether the system comprises monitor-specific host memories or a centralized host memory common to all monitors.

Figure 4:
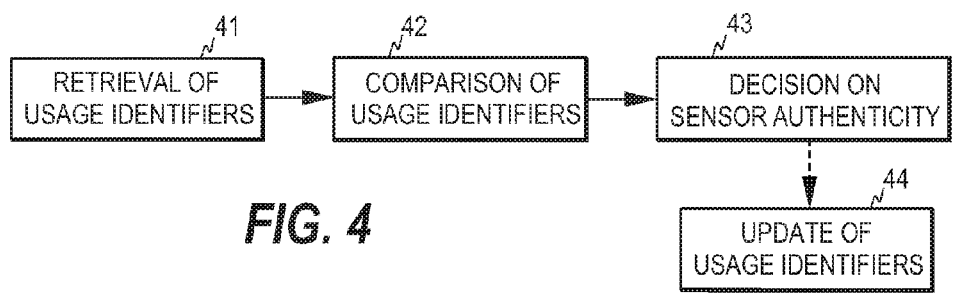
FIG. 4 illustrates an example of the functional units of the monitor unit in terms of the sensor authentication.

The control and processing unit, which is adapted to execute the sensor verification algorithm, may thus be seen, in terms of the sensor validation, as an entity of four operational modules or units, as is illustrated in FIG. 4: a retrieval unit 41 configured to retrieve the two usage identifiers in response to the connection of the sensor to the monitor, a comparison unit 42 configured to compare the two identifiers to determine whether or not the identifiers are consistent with each other, a decision-making unit 43 configured to make decision on the authenticity of the sensor and thus also on the permission/prohibition of the use of the sensor, and an update unit 44 configured to update the two identifiers in response to allowed use of the sensor.

A conventional patient monitor may be upgraded to enable the monitor to employ the above mechanism for authenticating a sensor connected to the monitor. Such an upgrade may be implemented, for example, by delivering to the monitor a software module that includes the sensor verification algorithm 107. The software module may be delivered, for example, on a data carrier, such as a CD or a memory card, or through a telecommunications network. The software module may be divided into four portions according to the above four operational units: a first program product portion configured retrieve, upon detected connection of a sensor to the patient monitor, the first and second usage identifier of the connected sensor, a second program product portion configured to examine whether the retrieved first and second usage identifiers of the connected sensor are consistent, a third program product portion configured to allow or reject the use of the connected sensor in response to the examination, and a fourth program product portion configured to update the first and second usage second usage identifiers of the connected sensor if the use of the connected sensor is allowed and/or if actual use is detected after the use is allowed.

The mechanism disclosed above thus keeps the sensor-specific usage identifiers in the sensor and in the host memory updated and consistent with each other. If a counterfeited sensor is connected to the monitor, it is highly likely that its usage identifier does not correspond to the usage identifier maintained in the host memory since the usage identifiers of an authorized sensor change according to the use of the authorized sensor. It is therefore difficult to introduce and use a counterfeited copy of the sensor. The above mechanism therefore provides an uncomplex solution for protecting the measurements against the drawbacks and risks related to unauthorized or counterfeited sensors.

Figure 5:
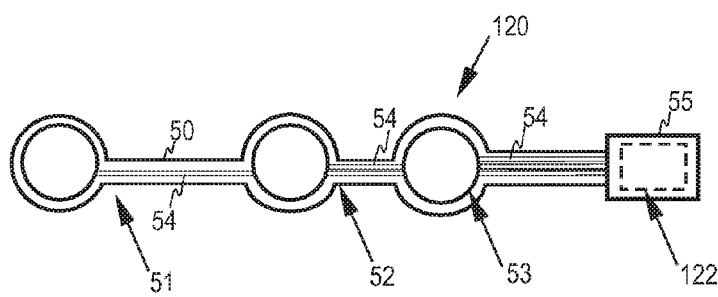
FIG. 5 illustrates one embodiment of a sensor that may be authenticated by the mechanism disclosed.

FIG. 5 is a top view of one embodiment of the sensor 120. The sensor comprises a thin and flexible substrate 50 made of plastic material, for example. The thickness of the substrate is typically below 0.5 mm. Three electrodes 51 to 53 are integrated onto the surface of the substrate, each electrode being provided with a respective connector 54 connecting the electrode to a terminal 55 at one end of the sensor. The connectors may be printed on the substrate and the terminal can be connected with a mating terminal of a measurement cable 130 (not shown). The terminal 55 also serves as a mounting platform for the sensor memory 122 so that when the terminal is connected to the mating terminal of the cable, a proper physical and electrical contact is formed between the sensor and the monitor. The portions of the substrate around the sensors may be provided with an adhesive coating for adhering the sensor to the skin of a subject. Since the authentication mechanism does not require any special features regarding the sensor memory, the sensor memory may be a generic memory with no customized areas/parts, associated intelligence, or data processing capability. Further, all sensor units may use similar generic memories.

The sensor unit may also be of non-electrode type, such as a pulse oximeter sensor that comprises a plurality of light emitters and a photo detector common to the light emitters. In this case, the control and processing unit supplies a drive current to the emitters, as is shown by the dashed line in FIGS. 1 and 3. However, as the electrode-type sensors according to FIG. 4 are easier to counterfeit, the protection mechanism disclosed finds most use in connection with sensors provided with electrodes, or other sensors that are rather uncomplex and vulnerable to illegal copying.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural or operational elements that do not differ from the literal language of the claims, or if they have structural or operational elements with insubstantial differences from the literal language of the claims.

The invention claimed is:

1. A method for authenticating a physiological sensor, the method comprising:
    examining, in response to a sensor being connected to a patient monitor, whether a first sensor-specific usage count of the connected sensor is greater than or equal to a second sensor-specific usage count of the connected sensor, wherein the first and second sensor-specific usage counts are indicative of cumulative usage of the connected sensor and wherein the first sensor-specific usage count is stored in the connected sensor and the second sensor-specific usage count is stored in a host memory external to the connected sensor;
    allowing use of the connected sensor in the patient monitor when the examining indicates that the first sensor-specific usage count is greater than or equal to the second sensor-specific usage count for the connected sensor;
    rejecting the use of the connected sensor in the patient monitor when the examining indicates that the first sensor-specific usage count is less than the second sensor-specific usage count of the connected sensor; and
    updating the first and second usage counts for the connected sensor in response to the use of the connected sensor in the patient monitor, thereby to keep the first and second sensor-specific usage counts of the connected sensor consistent and updated for a subsequent use attempt of the connected sensor.

2. The method according to claim 1, wherein the updating includes updating the first usage count stored in the connected sensor, in which the first usage count is stored in a generic memory of one of EEPROM and EPROM memory types.

3. The method according to claim 1, further comprising storing a fixed sensor-specific count in a plurality of sensors, wherein the storing is performed prior to use of the plurality of sensors and wherein the connected sensor is any of the plurality of sensors.

4. The method according to claim 3, further comprising
    encrypting the fixed sensor-specific count and the first sensor-specific usage count prior to the storing; and
    encrypting the first sensor-specific usage identifier prior to the updating.

5. The method according to claim 1, wherein the examining includes retrieving the second sensor-specific usage through a network.

6. The method according to claim 1, wherein the examining includes relieving the second sensor-specific usage count from the host memory, wherein the host memory is in the patient monitor.

7. The method according to claim 6, wherein the updating includes incrementing the first usage count and the second usage count, wherein the first usage count is indicative of total number of times the connected sensor is used and the second usage count is indicative of total number of times the sensor is used in the patient monitor.

8. A computer program product for authenticating a physiological sensor connected to a patient monitor, the computer program product comprising:

a first program product portion configured retrieve, upon connection of a sensor to a patient monitor, a first usage count of the connected sensor from said sensor and a second usage count of the connected sensor from a host memory external to the connected sensor, wherein the first and second usage counts are indicative of cumulative usage of the connected sensor;

a second program product portion configured to examine whether the retrieved first usage count is greater than or equal to the second usage count of the connected sensor;

a third program product portion configured to allow use of the connected sensor when the first usage count is greater than or equal to the second usage count and to reject the use of the connected sensor when the first usage count is less than the second usage count; and a fourth program product portion configured to update the first and second usage counts of the connected sensor in response to the use of the connected sensor, thereby to keep the first and second usage counts of the connected sensor consistent and updated for a subsequent use attempt of the sensor.

9. A method for authenticating a physiological sensor, the method comprising:

identifying the connection of the sensor to a patient monitor;

determining in the patient monitor a relationship between a first sensor-specific usage count and a second sensor-specific usage count for the connected sensor, wherein the first and second sensor-specific usage counts are indicative of cumulative usage of the connected sensor, wherein the first sensor-specific usage count is stored in the connected sensor and the second sensor-specific usage count is stored in a memory unit external to the connected sensor;

allowing use of the connected sensor with the patient monitor when the first sensor-specific usage count is greater than or equal to the second sensor-specific usage count;

rejecting the use of the connected sensor with the patient monitor when the first sensor-specific usage count is less than the second sensor-specific usage count; and updating the first and second sensor-specific usage counts upon the authorized use of the connected sensor with the patient monitor.

10. The method according to claim 9 further comprising the steps of storing a fixed sensor-specific count in a plurality of sensors, wherein the fixed sensor-specific count is stored in the plurality of sensors prior to use of any of the plurality of sensors.

11. The method according to claim 9 wherein the examining step includes retrieving the second sensor-specific usage count through a network.

12. The method according to claim 9 wherein the examining includes retrieving the second sensor-specific usage count from the host memory, wherein the host memory is in the patient monitor.

13. The method according to claim 12, wherein the updating includes incrementing the first usage count the second usage count, wherein the first usage count is indicative of total number of times the connected sensor is used and the second usage count is indicative of total number of times the sensor is used in the patient monitor.

* * * * *